United States Patent [19]
Kakiuti

[11] Patent Number: 5,741,236
[45] Date of Patent: Apr. 21, 1998

[54] PREFILL SYRINGE

[75] Inventor: Makoto Kakiuti, Takahagi, Japan

[73] Assignee: Arte Corporation, Tokyo, Japan

[21] Appl. No.: 665,015

[22] Filed: Jun. 11, 1996

[30] Foreign Application Priority Data

| Jun. 16, 1995 | [JP] | Japan | 7-150748 |
| Nov. 28, 1995 | [JP] | Japan | 7-309594 |
| Feb. 14, 1996 | [JP] | Japan | 8-027156 |

[51] Int. Cl.$^6$ ............................................. A61M 5/32
[52] U.S. Cl. .................... 604/192; 604/199; 604/263
[58] Field of Search .................................. 604/181, 187, 604/192, 199, 218, 232, 234, 263

[56] References Cited

U.S. PATENT DOCUMENTS

| 4,365,626 | 12/1982 | House | 128/218 DA |
| 4,636,201 | 1/1987 | Ambrose et al. | 604/192 |
| 4,664,653 | 5/1987 | Sagstetter et al. | 604/197 |
| 4,897,083 | 1/1990 | Martell | 604/192 |
| 4,986,818 | 1/1991 | Imbert et al. | 604/192 |
| 5,147,325 | 9/1992 | Mitchell et al. | 604/192 |
| 5,263,933 | 11/1993 | Novacek et al. | 604/110 |

FOREIGN PATENT DOCUMENTS

| 0568207 | 11/1993 | European Pat. Off. . |
| 5-16657 | 3/1993 | Japan . |
| 9628201 | 3/1996 | WIPO . |

*Primary Examiner*—Michael Buiz
*Assistant Examiner*—Deborah Blyveis
*Attorney, Agent, or Firm*—Jacox, Meckstroth & Jenkins

[57] ABSTRACT

The present invention relates to a prefill syringe in which the space provided at the joining area between a cap or protector and a needle holder can be covered by an inexpensive material and a simple method, without interrupting the flow of the production process. In this prefill syringe, a cap 15 or a protector is attached to a needle holder 11 provided to one end of cartridge 10, and a cylindrical member 20 formed of an elastic material is externally engaged to span the needle holder and cap or protector so as to cover the joining area A between the needle holder and the cap, or the joining area between the needle holder and the protector. Further, one or more ring-shaped projections which contact the outer peripheral surface of the needle holder and the outer peripheral surface of the cap are formed to the inner periphery of the cylindrical member.

20 Claims, 6 Drawing Sheets

PREFILL SYRINGE

BACKGROUND OF THE INVENTION

1. Field of the Invention

The present invention relates to a prefill syringe wherein the syringe cartridge is prefilled with a drug and a rubber stopper is inserted into the cartridge to hermetically seal the drug therein.

2. Description of the Related Art

As the name implies, a prefill syringe is designed to reduce the time and trouble associated with the use of a syringe by providing a syringe which has been prefilled with a drug and completely sterilized prior to shipping by a pharmaceutical company. Thus, such a syringe can be used immediately.

A prefill syringe of this design functions not only as a syringe, but also as a container for holding a drug over a long period of time. Accordingly, as in the case of a vial and ampoule, it is not only necessary to completely sterilize the container prior to filling with the drug, but it is also desirable to carry out a final sterilization of the prefilled syringe after it has been filled with the drug and sealed in order to complete sterilization during the production process.

Figure 13:
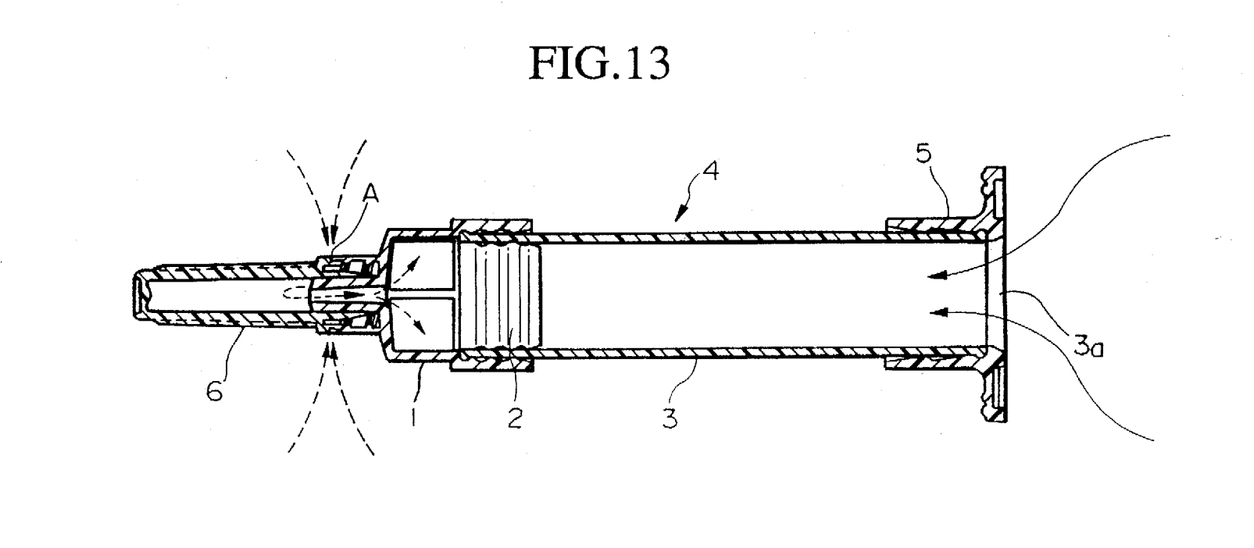
FIG. 13 is a cross-sectional diagram of the cartridge in a conventional prefill syringe.

However, as shown in FIG. 13, in a prefill syringe 4 in which a syringe needle is attached to a needle holder 1 and a rubber stopper 2 is set inside a cartridge 3, ethylene oxide gas or vapor used in a gas or vapor sterilization treatment that is performed to the empty container before it is filled with a drug enters through opening 3a at the collar 5 end (i.e., the end opposite needle holder 1) of the prefill syringe, as indicated by the solid arrow lines in the figure. However, because the inside of cartridge 3 is sealed in an air and liquid tight fashion by the peaked, or outwardly projecting, portion, of rubber stopper 2, the flow of ethylene oxide gas toward needle holder 1 is blocked. As a result, the area from rubber stopper 2 to needle holder 1, or the area from rubber stopper 2 to the syringe needle portion, cannot be sterilized.

In order to resolve this problem, the area of joining between needle holder 1 of cartridge 3 and cap 6, or alternatively, the area of joining between the needle holder and a protector covering the syringe needle, is designed to permit the passage of gases from the external environment.

In other words, in the case of shipping syringes without attached syringe needles, a small interval of space is provided so that the area A of joining between cap 6 and needle holder 1 does not become airtightly sealed. Likewise, in the case of shipping syringes having an attached syringe needle, a small interval of space is provided so that the area A of joining between the syringe needle protector and the needle holder does not become airtightly sealed. Vapor or ethylene oxide gas enters into needle holder 1 through this interval of space as indicated by the dashed arrow lines in FIG. 13. As a result, the area from rubber stopper 2 to needle holder 1 (or the syringe needle portion) can be sterilized.

Further, by providing the structure disclosed in "Package Sealing Portion for Sterilized Medical Devices" (Japanese Utility Model Laid Open Publication No. Hei 5-16657) to the inner side of a cap or protector, contamination from the plastic or through the space between the needle holder and a protector during the filling operation can be prevented. As a result, it is not necessary to again sterilize this area after filling.

Each part of cartridge 3 sterilized in this way prior to filling remains sterile after filling with the drug. Thus, post-filling sterilization is necessary only for those parts of cartridge 3 which come in contact with the drug, or for parts added or attached during the filling process. Other parts of cartridge 3 need not be sterilized again.

However, when the drug filling the cartridge is sterilized for a final time after filling by heating the cartridge with vapor or hot water from the outside, the vapor or hot water can enter the syringe via the space provided at joining area A between cap 6 and needle holder 1, or between the protector and needle holder 1. Thus, bacterial contamination can subsequently occur in any moisture which might remain inside the cartridge. Further, as in the case of drying an empty syringe prior to filling, the entire syringe (cartridge) containing the drug must be treated over a long period of time with high temperature dry air to remove this moisture through sufficient drying. Thus, depending on the type of drug being used in the syringe, the effect of this high temperature on the drug may be a cause for concern. For this reason, in order to carry out post-filling sterilization on a prefill syringe which has undergone sterilization prior to filling, it is necessary to employ some sort of method to cover the space at joining area A.

Moreover, it is necessary that the method for sealing this type of space be one which does not interrupt the flow of the filling process, employs an inexpensive material which is suitable for a disposable prefilled syringe, and is simple. These requirements have accordingly presented considerable obstacles to the realization and wide-scale use of a prefill syringe.

SUMMARY OF THE INVENTION

The present invention was conceived in consideration of the aforementioned problems, and has as its objective the provision of a prefill syringe in which a space that is provided between the needle holder and a cap or protector for vapor or gas sterilization is covered by means of an inexpensive material and a simple method which do not interrupt the flow of the production process. As a result, the influx of vapor or hot water through the space at the area of joining between the needle holder and the cap or protector is prevented during a sterilization performed subsequent to drug filling.

The present invention is provided with a cylindrically shaped cartridge into which a rubber stopper is inserted, the cartridge having a needle holder at one end and a collar at the other end thereof. A protective cap is attached to the cartridge's needle holder, with a cylindrical member consisting of an elastic material engaged externally to span from the needle holder to the cap so as to cover the area of joining therebetween.

The inner periphery of this cylindrical member may be provided with one or more ring-shaped projections which contact the outer peripheral surfaces of the needle holder and the cap.

This cylindrical member may be formed in the shape of a sheath having one end sealed and the other end open.

Further, a communicating hole which communicates the inside of the cylindrical member with the outside environment may be formed in the sealed end of the sheath-shaped cylindrical member.

A seal which engages in an air tight fashion about the circumference of the tip of the cap may be formed to the communicating hole formed at the sealed end of the sheath-shaped cylindrical member.

Further, this cylindrical member may be formed in the shape of a tube, with both ends open.

A syringe needle is attached to the needle holder, and a protector which covers the syringe needle may be attached to the needle holder in place of a cap. A cylindrical member consisting of an elastic material is externally engaged to span between the needle holder and the protector so as to cover the area of joining between the needle holder and the protector. One or more ring-shaped projections which are in contact with the outer peripheral surfaces of the needle holder and the protector may be formed to the inner peripheral surface of the cylindrical member. Moreover, this cylindrical member is characterized in that one end is sealed while the other end is open.

A stepped portion may be provided at a point along the length of the outer periphery of the cylindrical member. The diameter at the tip of the cylindrical member, and the diameter extending between the outer edges of the stepped portion may differ.

In the present invention, a cylindrical member consisting of an elastic material is engaged externally to span between the needle holder and the cap so as to cover the area of joining therebetween. Thus, the space provided at the area of joining between the cap and the needle holder can be covered in an air and liquid tight fashion without interrupting the flow of the production process. As a result, the influx of vapor or hot water through the space at this area of joining during the sterilization process after the cartridge has been filled with the drug can be prevented.

Further, the syringes are packed without removing the elastic cylindrical member in a subsequent production step. Thus, the cylindrical member can be used as to augment grippability when removing the cap at time of use.

By forming one or more ring-shaped projections to the inner periphery of the cylindrical member which are in contact with the outer peripheral surfaces of the needle holder and the cap, the air and liquid tight seal between the cylindrical member and the needle holder or cap can be improved even further. Moreover, because there is little friction when inserting and disposing the cylindrical member, operability is improved.

By forming the cylindrical member in the shape of a sheath wherein one end is sealed and the other is open, errors in the direction of insertion of the cylindrical member are eliminated, since the end of the cylindrical member provided with the ring-shaped projections is always inserted first.

By providing a communicating hole to the sealed end of a sheath-shaped cylindrical member for communicating the inside of the cylindrical member with the external environment, the exertion of an upward force on the cylindrical member due to the expansion of air remaining inside the cylindrical member as the temperature inside the cylindrical member increases during vapor sterilization does not occur. Thus, the cylindrical member does not shift in position, nor is there any deterioration in the quality of the seal between the cylindrical member and the needle holder.

Once the cylindrical member has been attached so as to cover the engagement between the cap and the needle holder, then even if a space arise between the outer sides of the cap and the inner peripheral surface of the cylindrical member due to the presence of vertical ribs formed to the outer periphery of the cap for example, it is possible to prevent vapor or the like from entering through this space during a vapor sterilization process carried out following drug filling.

By forming the cylindrical member in the shape of a tube with both ends open, the size of the cylindrical member can be minimized as necessary, thus reducing weight and cutting material costs.

By providing a stepped portion to the outer periphery of the cylindrical member, the stepped portion can be used for readily catching or moving the cylindrical member mechanically. Thus, the steps in the production process can be simplified. Further, when inserting the cylindrical member into the area of joining between the needle holder and the cap, or into the area of joining between the needle holder and the protector, the stepped portion can be employed as a measure of the degree of insertion of the cylindrical member.

BRIEF DESCRIPTION OF THE DRAWINGS

FIG. 1 shows the components of a prefill syringe according to the first embodiment of the present invention, where

FIG. 7 shows a prefill syringe according to the sixth embodiment of the present invention, where

DESCRIPTION OF THE PREFERRED EMBODIMENTS

An explanation will now be made of each of the embodiments of the present invention, with reference being given to the figures.

<First Embodiment>

Figure 1A:
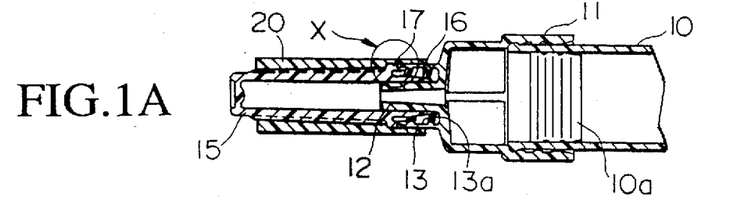
FIG. 1A shows the prefill syringe in vertical cross-section and FIG. 1B shows an enlargement of the area enclosed in the circle indicated by X in FIG. 1A.
Figure 1B:
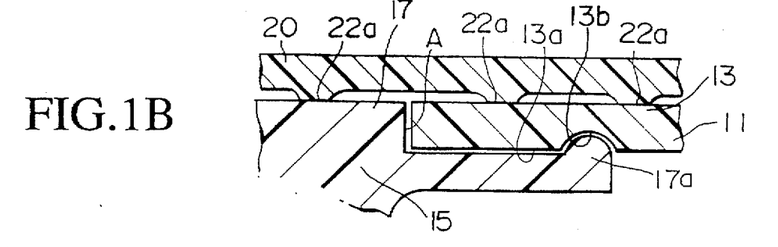
Figure 2:
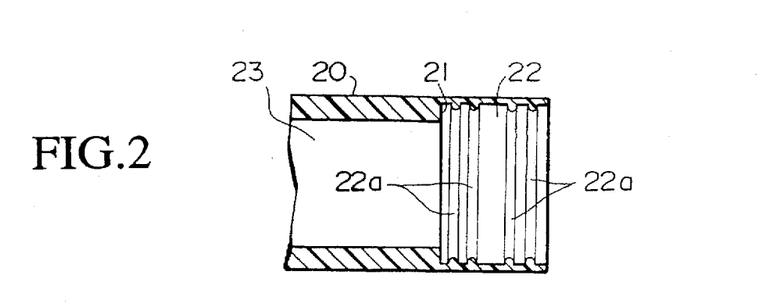
FIG. 2 is an enlarged cross-sectional diagram of the principle components of the cylindrical member according to the first embodiment.

FIGS. 1 and 2 show a portion of the cartridge which composes a preloaded syringe according to the first embodiment of the present invention. Cartridge 10 is cylindrically shaped, with a needle holder 11 provided to one end and a collar provided to the other end thereof. Further, a rubber stopper 10a is inserted to be set inside cartridge 10. Note that FIG. 1A shows only one end of cartridge 10, while the other end of the cartridge and the plunger rod or the like inserted in the cartridge are omitted.

Figure 5:
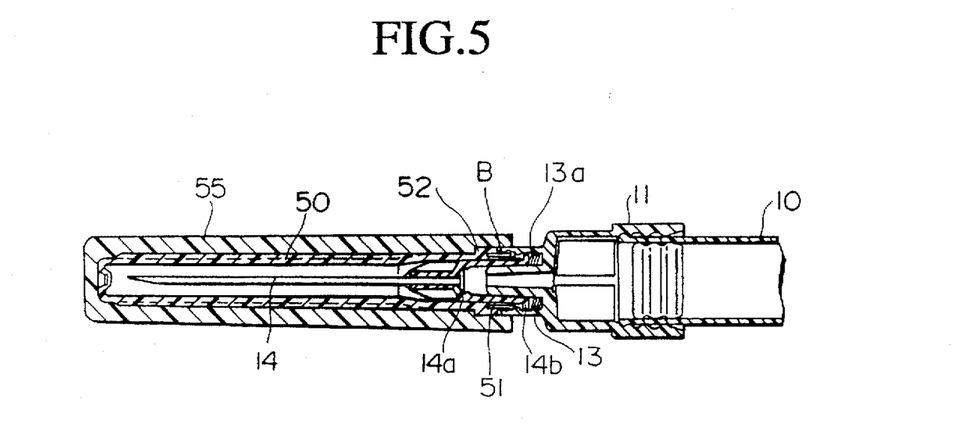
FIG. 5 is a diagram in cross-section of the principle components of a prefill syringe according to the forth embodiment of the present invention.

A nozzle 12 and a collar 13 which is disposed external to and concentrically about nozzle 12 are provided to needle holder 11 of cartridge 10. A thread 13a is formed to the inner periphery of collar 13. As shown in FIG. 5, a flange 14b formed to the needle base 14a of syringe needle 14 engages with this thread 13a during use.

A cap 15 is attached to needle holder 11 to maintain nozzle 12 in a sterile state. Cap 15 is provided with an attaching engagement 16 which overlaps the external periphery of nozzle 12 while still permitting the passage of gas, and a flange 17 which is provided projecting outward from attaching engagement 16. When flange 17 abuts the tip of collar 13 of needle holder 11, so that the outer peripheral surfaces of flange 17 and collar 13 lay in roughly the same plane, one or plural projections 17a which is provided protruding at the tip of flange 17 engages with an inner peripheral groove 13b at the end of collar 13. As a result cap 15 is engaged and fixed to needle holder 11.

A small space is formed at the joining area A between needle holder 11 and cap 15. A cylindrical member 20 is engaged eternally to span needle holder 11 and cap 15 so as to cover joining area A where this space is provided.

Cylindrical member 20 is composed of a suitably elastic material such as rubber, and is formed in the shape of a tube which is open at both ends. As shown in FIG. 2, a stepped portion 21 is formed at a point along the inner periphery of cylindrical member 20 in a shape which corresponds with the shape of cap 15. In FIG. 2, the right side of the inner periphery of stepped portion 21 forms a large diameter portion 22, while the left side of the inner periphery of stepped portion 21 forms a small diameter portion 23. A plurality of ring-shaped projections 22a are formed at intervals to inner peripheral large diameter portion 22, with the spacing interval between ring-shaped projections 22a particularly wide at the center of inner peripheral large diameter portion 22. Ring-shaped projections 22a come in contact with the outer peripheral surfaces of needle holder 11 and cap 15, respectively, with each of these outer peripheral surfaces being in contact with at least one ring-shaped projection 22a respectively. In this embodiment, a total of 4 ring-shaped projections are formed, two contacting the outer peripheral surface of needle holder 11 and two contacting the outer peripheral surface of cap 15.

The inner diameter of inner peripheral large diameter portion 22 of cylindrical member 20 is designed to be slightly larger than the outer diameters of needle holder 11 and cap 15. Moreover, the inner diameter of ring-shaped projections 22a inside inner peripheral large diameter portion 22 is designed to be slightly smaller than the outer diameters of needle holder 11 and cap 15.

The function of a prefilled syringe of the above described structure will now be explained.

In the actual drug filling process, as a general example, a prefill syringe in which a cap 15 is attached to a needle holder 11 undergoes a vapor or gas sterilization prior to filling with a drug. After sufficiently sterilizing the inside of needle holder 11, the prefill syringe is filled with a drug, and cylindrical member 20 is inserted over the tip of cap 15.

At this point, the entire inner peripheral surface of cylindrical member 20 does not adhere to the outer peripheral surfaces of cap 15 and needle holder 11. Rather, by means of the ring-shaped projections 22a alone, which are provided on the inner periphery of cylindrical member 20, the outer surfaces of both cap 15 and needle holder 11 are held tightly. Thus, friction upon insertion of the cylindrical member 20 is minimized, with the result that a smooth insertion can be accomplished mechanically without the intervention of human labor.

Cylindrical member 20 is inserted over the tip of cap 15. By inserting cylindrical member 20 to a position where a number of the ring-shaped projections 22a at the base end of the cap pass beyond the joining area A between needle holder 11 and cap 15, each of the ring-shaped projections 22a come in contact with either the outer periphery of cap 15 or the outer periphery of needle holder 11 so that cylindrical member 20 spans joining area A between cap 15 and needle hold 11. As a result, the joining area A between cap 15 and needle holder 11 is completely sealed.

As a result, even if the prefill syringe is transferred to a vapor or hot water sterilization step after filling, the influx of vapor or hot water through the joining area A between cap 15 and needle holder 11 is prevented. Thus, it becomes possible to perform a sterilization process the cartridge has been filled with the drug.

Further, by setting a cylindrical member 20 of this type on cap 15, cap 15 is provided with a outer diameter which is sufficiently large enough to permit easy grasping with the fingers even in the case where cartridge 10 itself has an extremely small diameter. As a result, cap 15 is easily removed at time of use, with cylindrical member 20 augmenting the ease of removal of the cap. Thus, the attachment of cylindrical member 20 to the cap after sterilization does not present a hindrance to shipment of the prefilled syringe. Accordingly, it is not necessary to provide a step to remove cylindrical member 20.

<Embodiment 2>

Figure 3:
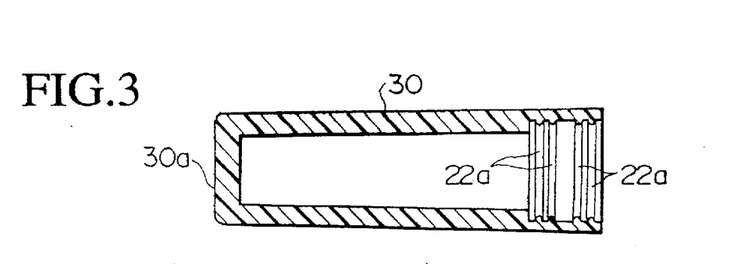
FIG. 3 is a diagram in vertical cross-section of the cylindrical member according to the second embodiment of the present invention.

FIG. 3 shows a second embodiment of the present invention. The same numerals have been employed here where components are identical to those in the first embodiment, and an explanation thereof has been omitted. This practice will be employed in the case of subsequent embodiments, as well.

The rubber cylindrical member 30 shown here is formed in the shape of a sheath, sealed at one end and open at the other. The length of cylindrical member 30 is such that the sealed end 30a of cylindrical member 30 does not interfere with the tip of cap 15 when it is set over the cap, thereby bringing the ring-shaped projections 22a provided to the inner periphery at the base end of the cylindrical member 30 into contact with the outer peripheral surfaces of the needle holder and the cap so that cylindrical member 30 spans the joining area between the needle holder and the cap.

As in the first embodiment, the entire inner surface of cylindrical member 30 does not adhere with the outer peripheral surfaces of cap 15 and needle holder 11 in this embodiment either. Rather, tight binding is accomplished by means of the ring-shaped projections 22a alone. As a result, cylindrical member 30 can be smoothly inserted mechanically over the cap, to prevent the influx of vapor or water droplets through the area of joining between the cap and the needle holder during a final sterilization process. Moreover, if cylindrical member 30 is grasped from above with the fingers when removing the cap, then, as was the case when employing a cylindrical member 20, cap 15 can be easily removed.

<Embodiment 3>

Figure 4:
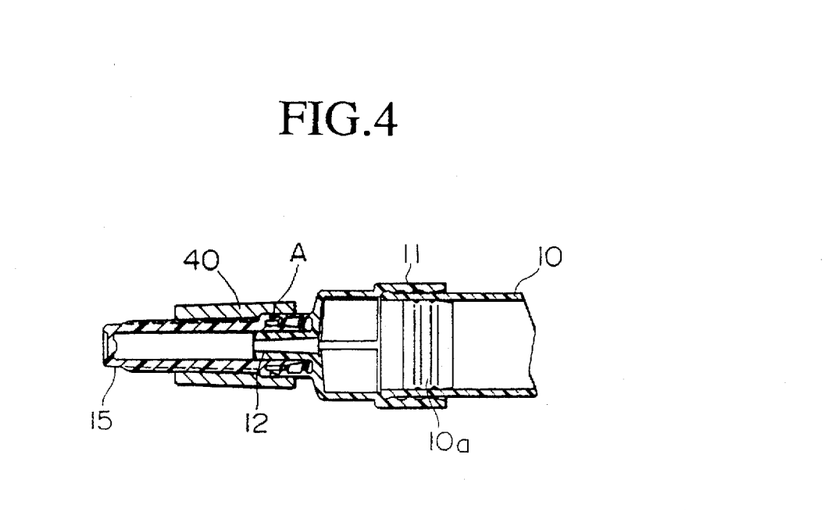
FIG. 4 is a diagram in vertical cross-section of the principle components of the prefill syringe according to the third embodiment of the present invention.

FIG. 4 shows a third embodiment of the present invention.

As in the case of the cylindrical member 20 of the first embodiment, the cylindrical member 40 shown here is formed in the shape of a tube, open at both ends. However, this cylindrical member 40 is shorter than cylindrical member 20. Further, a plurality of ting-shaped projections are formed at intervals to the inner periphery of cylindrical member 40, as in the first and second embodiments.

By making cylindrical member 40 shorter, its insertion over the tip of cap 15 is facilitated in the case where cap 15 is comparatively long. Further, the material costs associated with cylindrical member 40 are reduced.

In other words, because both ends of cylindrical member 40 are open, when cylindrical member 40 is inserted over the tip of cap 15 for cartridge 10, such that a number of the ring shaped projections formed to the inner surface of cylindrical member 40 pass beyond the area of joining between needle holder 11 and cap 15, then the ring-shaped projections are in contact with the peripheral surfaces of cap 15 and needle holder 11 in the vicinity of the area of joining therebetween. Thus, needle holder 11 and cap 15 are tightly held, with ring-shaped projections 22a spanning the joining area A therebetween.

As in the first embodiment, the entire inner surface of the cylindrical member 40 does not adhere with the outer peripheral surfaces of cap 15 and needle holder 11. Rather, since the restraint is accomplished merely by means of ring-shaped projections 22a, cylindrical member 40 can be smoothly inserted mechanically. Further, an influx of water droplets through joining area A during a shower sterilization can be prevented. Moreover, at time of use of the prefill syringe, cap 15 can be removed easily by grasping cylindrical member 40 between the fingers and pulling it off, thereby pulling off the cap as well.

<Embodiment 4>

FIG. 5 shows a fourth embodiment of the present invention.

In this fourth embodiment, a flange 14b formed to the needle base 14a screws together with a screw 13a on the inner periphery of collar 13, thereby attaching a syringe needle 14 to needle holder 11 prior to filling. In this embodiment, a protector 50 for protecting syringe needle 14 is employed in place of a cap. Protector 50 is attached to needle holder 11 such that an attaching engagement 51 at the base of protector 50 is joined to the outer periphery of needle base 14a under frictional force, while a flange 52 provided external to attaching engagement 51 lies opposite the tip of collar 13 of needle holder 11 with an interval of space present therebetween. In addition to joining the protector about the outer periphery of needle base 14a of syringe needle 14, other methods of attachment of protector 50 to needle holder 11 are available. For example, as in the first embodiment, one or plural projections provided at the tip of protector 50 may be engaged in inner periphery grooves 13b at the tip of collar 13.

A suitably elastic cylindrical member 55 is externally engaged to the area B of joining between needle holder 11 and protector 50, spanning it. Cylindrical member 55 is formed in the shape of a sheath with an inner diameter which is identical to or slightly larger than the outer diameters of collar 13 and protector 50 of needle holder 11. As in all of the preceding embodiments, a plurality of ring-shaped projections 22a are formed to the inner periphery of cylindrical member 55 with an interval of spacing therebetween. Further, when cylindrical member 55 is externally engaged to needle holder 11 and protector 50 so as to span the area of joining therebetween, ring-shaped projections 22a come in contact with the outer peripheral surfaces of needle holder 11 and protector 50 respectively, to seal joining area B.

In this prefill syringe, a prefill syringe with an attached syringe needle 14 undergoes vapor or gas sterilization prior to filling with a drug. Cartridge 10 is then filled with a drug, and cylindrical member 55 is inserted to a position where a number of the ring-shaped projections 22a formed to its inner periphery span the joining area B between needle holder 11 and protector 50, this operation being carried out without interruption to the production process.

As in the first embodiment, the entire surface of cylindrical member 55 does not adhere with the outer peripheral surfaces of protector 50 and needle holder 11. Rather, restraint is accomplished by means of the ring-shaped projections only, thus cylindrical member 55 can be smoothly inserted mechanically. Moreover, protector 50 can be easily removed together with cylindrical member 55 by grasping cylindrical member 55 between the fingers and pulling it off.

<Embodiment 5>

Figure 6:
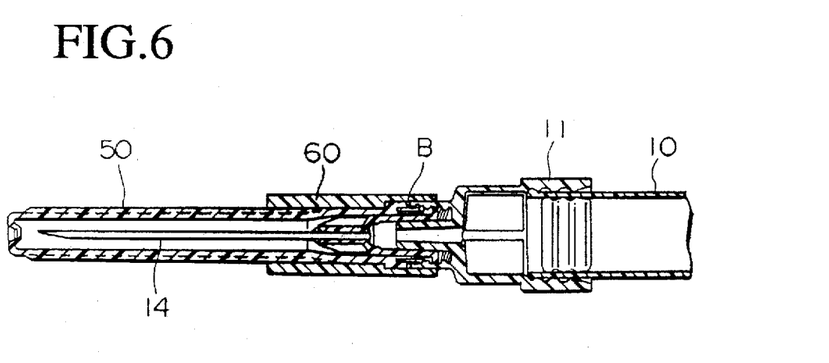
FIG. 6 is a diagram in vertical cross-section of the principle components of a prefill syringe according to the fifth embodiment of the present invention.

FIG. 6 shows a fifth embodiment of the present invention.

In this embodiment, a cylindrical member 60 which is externally engaged to span across needle holder 11 and protector 50 so as to cover the joining area B therebetween is formed in the shape of a tube, with both ends open, rather than in the shape of a sheath as in the fourth embodiment shown in FIG. 5.

In this embodiment, the preloaded syringe with attached syringe needle 14 undergoes a gas or vapor sterilization prior to filling with the drug. The cartridge is then filled with the drug, and cylindrical member 60 is inserted to a position where it covers the joining area B between needle holder 11 and protector 50. These operations are carried out mechanically in a smooth fashion, without interruption to the production process.

<Embodiment 6>

Figure 7A:
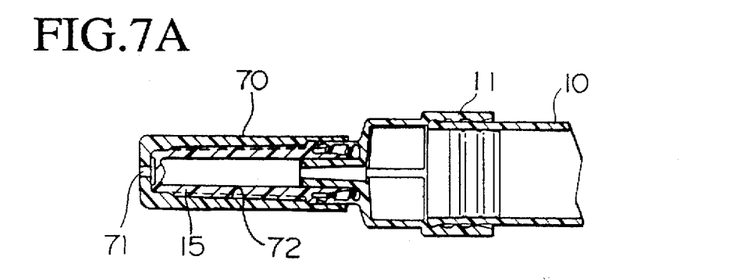
FIG. 7A shows the prefill syringe in vertical cross-section and FIG. 7B shows the cylindrical member in cross-section.

FIG. 7 shows a sixth embodiment of the present invention.

Figure 7B:
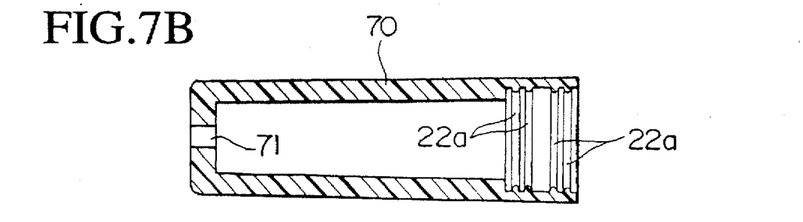

In this embodiment, cylindrical member 70 which engages to span between needle holder 11 and cap 15 is formed in shape of a sheath, with one end sealed and the other open.

Further, a communicating hole 71 is formed in the approximate center of the closed end of cylindrical member 70 for communicating the inside of cylindrical member 70 with the outside environment.

In this embodiment, as in the previous embodiments, ring-shaped projections 22a formed to the inside of cylindrical member 70 adhere to the outer peripheral surfaces of cap 15 and needle holder 11. As a result, the influx of water droplets or the like through joining area A during a shower sterilization can be prevented with certainty. Moreover, cap 15 can be removed easily at time of use by gripping cylindrical member 70 between the fingers and removing it along with cap 15.

Further, in this embodiment, the area inside cylindrical member 70, namely the space 72 enclosed by the inner peripheral surface of cylindrical member 70 and the outer peripheral surface of the cap, is open to the external environment via communicating hole 71. Thus, even when the temperature inside cylindrical member 70 increases during a vapor sterilization, there is no upward force applied on cylindrical member 70 by expanding air since air does not remain inside space 72. Thus, there is no concern that the seal between cylindrical member 70 and needle holder 11 and the like will deteriorate due to a shift in the position of cylindrical member 70 caused by increasing pressure from expanding air.

<Embodiment 7>

Figure 8:
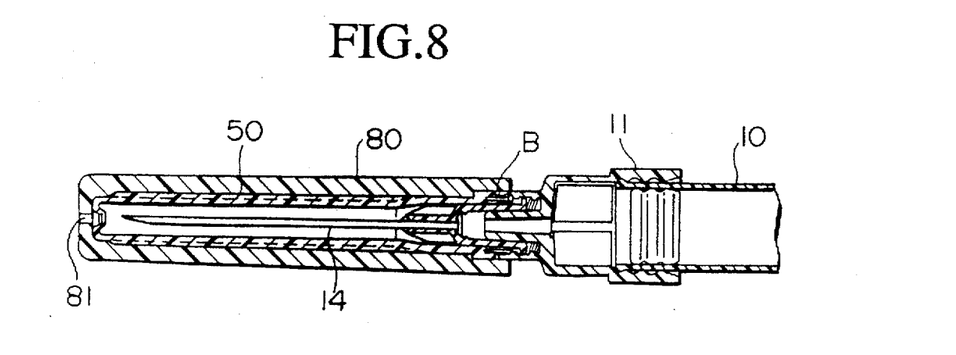
FIG. 8 shows a prefill syringe according to the seventh embodiment of the present invention, wherein the principle components of the prefill syringe are shown in vertical cross-section.

FIG. 8 shows a seventh embodiment of the present invention.

In this embodiment, a cylindrical member 80 is externally engaged to span the joining area B between needle holder 11 and protector 50. As in the previous embodiments, a plurality of ring-shaped projections are formed to the inner periphery of cylindrical member 80 with an interval of spacing therebetween. Further, a communicating hole 81 which communicates the inside of cylindrical member 80 with the outside environment is formed at the approximate center of the sealed end of cylindrical member 80.

As in embodiment 6, in this embodiment the ring-shaped projections formed to the inside of the cylindrical member 80 adhere to the outer peripheral surfaces of cap 15 and needle holder 11. Thus, the influx of water droplets through joining area B between needle holder 11 and protector 50 is prevented with certainty. Moreover, even when the temperature inside cylindrical member 80 increases during a vapor sterilization, there is no upward force applied on cylindrical member 80 by expanding air remaining inside the member. Thus, there is no concern that the seal between cylindrical member 80 and needle holder 11 and the like will deteriorate due to a shift in the position of cylindrical member 80.

<Embodiment 8>

Figure 9:
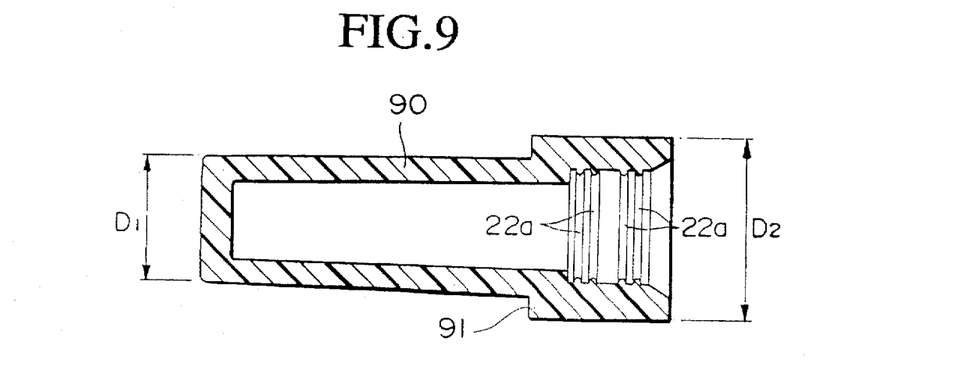
FIG. 9 is a diagram shown in vertical cross-section of the cylindrical member according to the eighth embodiment of the present invention.

FIG. 9 shows an eighth embodiment of the present invention.

In this embodiment, a stepped portion 91 is formed midway along the length of the outer periphery of a robber cylindrical member 90 which may be formed in the shape of the sheath or tube explained in the first through seventh embodiments above (FIG. 9 shows the case where cylindrical member 90 is formed in the shape of a sheath). The diameter D1 at the tip of cylindrical member 90, and the diameter D2 which extends between the outer edges of stepped portion 91 differ, with diameter D2 being larger than diameter D1.

Additionally, the provision of a plurality of ring-shaped projections 22a formed to the inner periphery of cylindrical member 90 with spacing therebetween is identical to that in the previous embodiments.

In this design wherein a stepped portion 91 is provided to the outer periphery of cylindrical member 90, stepped portion 91 can be employed to permit ready catching or transfer of cylindrical member 90 mechanically. As a result, the production process can be simplified. Further, when cylindrical member 90 is inserted into the area of joining between the needle holder and the cap, or the area of joining between the needle holder and a protector, stepped portion 91 can be employed as a standard to judge the extent of insertion of cylindrical member 90.

<Embodiment 9>

Figure 10:
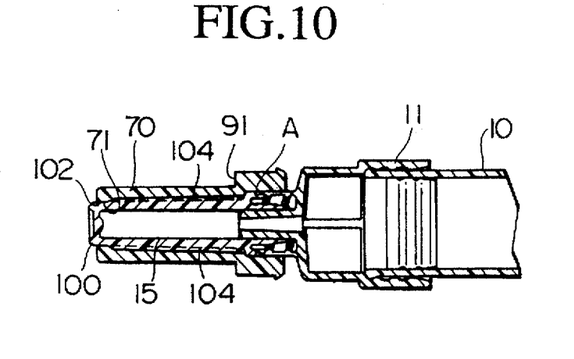
FIG. 10 shows the prefill syringe according to the ninth embodiment of the present invention, wherein the principle components of the prefill syringe are shown in vertical cross-section.

FIG. 10 shows a ninth embodiment of the present invention.

In this embodiment, a seal 102 is provided to communicating hole 71 formed at the sealed end of the cylindrical member 70 of the sixth embodiment shown in FIG. 7. Seal 102 engages with the circumferential portion 100 at the tip of cap 15 in an airtight fashion.

Taking into consideration interference, the inner diameter of communicating hole 71 of cylindrical member 70 prior to attachment is identical to or slightly smaller than the outer diameter of circumferential portion 100 at the tip of cap 15. Seal 102 is composed of the entire area of the inner periphery of communicating hole 71.

In other words, a plurality of vertical ribs 104, ... which project outward are formed to the external periphery of cap 15 about the circumference thereof. However, these vertical ribs 104, ... are not formed to extend to the tip of cap 15. Rather, the tip of cap 15 is formed in a simple circular shape.

In the embodiment shown here, the inner peripheral surface of communicating hole 71 is pressed against the outer periphery of this simple circular portion, to form the seal between cap 15 and cylindrical member 70.

The design of this embodiment compensates for the drawbacks present in the sixth embodiment of the present invention shown in FIG. 7.

In other words, in the present invention's sixth embodiment in FIG. 7, the space 72 enclosed by the inner peripheral surface of cylindrical member 70 and the outer peripheral surface of cap 15 is open to the outside via communicating hole 71. As a result, air does not become trapped in space 72, making it possible to prevent the exertion of an upward force on cylindrical member 70 due to expansion of air trapped in space 72 when the temperature rises during a sterilization process or the like. However, in this case, the following disadvantages could arise. Namely, the inner peripheral surface of cap 15 is lifted outward by vertical ribs 104, ... formed to the outer sides of cap 15. As a result, a space occurs between the outer sides of cap 15 and the inner peripheral surface of cylindrical member 70, causing loss of the airtight seal. Then, during vapor sterilization following filling with the drug, vapor or hot water could enter via communicating hole 71 and the space between the outer sides of cap 15 and the inner peripheral surface of cylindrical member 70, reaching joining area A between needle holder 11 and cap 15 and entering into needle holder 11.

However, in this ninth embodiment, in addition to providing a communicating hole 71 to communicate the space 72 enclosed between the inner peripheral surface of cylindrical member 70 and the outer peripheral surface of cap 15 with the external environment, a seal 102 which engages in an airtight manner with the circumferential portion 100 at the tip of cap 15 is provided to communicating hole 71. Accordingly, after cylindrical member 70 has been attached so as to cover the area of engagement between cap 15 and needle holder 11, the influx of vapor or hot water from the outside via a space which may arise between the outer sides of cap 15 and the inner peripheral surface of cylindrical member 70 due to vertical ribs 104, ... is prevented. In other words, the design of this embodiment makes it possible to eliminate air remaining inside space 72, while preventing the influx of vapor from the outside.

Additionally, a stepped portion 91 has been provided to the outer periphery of cylindrical member 70.

<Embodiment 10>

Figure 11:
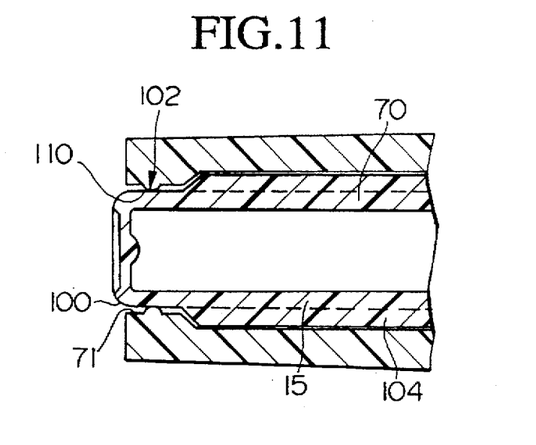
FIG. 11 shows the prefill syringe according to the tenth embodiment of the present invention, wherein the principle components are in cross-section to show the relationship between the cylindrical member and the cap.

FIG. 11 shows a tenth embodiment of the present invention.

In this embodiment, the provision of a seal 102 to communicating hole 71 formed at the sealed end of a sheath-shaped cylindrical member 70 is identical to embodiment 9. However, the substantial difference in this embodiment is that seal 102 is formed of a ring-shaped projection 110 that is formed to the inner peripheral surface of communicating hole 71.

As in the previous embodiment, in this embodiment as well, once cylindrical member 70 has been attached so as to cover the area of engagement between cap 15 and needle holder 11, the influx of vapor or hot water during vapor sterilization from the outside via a space which may arise between the outer sides of cap 15 and the inner peripheral surface of cylindrical member 70 due to vertical ribs 104, ... is prevented.

In the ninth embodiment shown in FIG. 10, the seal is composed of the entire area of the inner peripheral surface of communicating hole 71. For this reason, the dimensions of the inner diameter of communicating hole 71 and the outer diameter of the circumferential portion 100 at the tip of cap must be carefully controlled in order to ensure an excellent airtight seal therebetween. However, in the tenth embodiment shown here, seal 102 is formed by a ring-shaped projection 110 which permits a wide range of permissible variations in form. Thus, in this embodiment, strict regulation of the relationship between the dimensions of the inner diameter of communicating hole 71 and the outer diameter of the circumferential portion of the tip of cap 15 is not necessary; rather comparatively loose control of these dimensions is sufficient.

<Embodiment 11>

Figure 12:
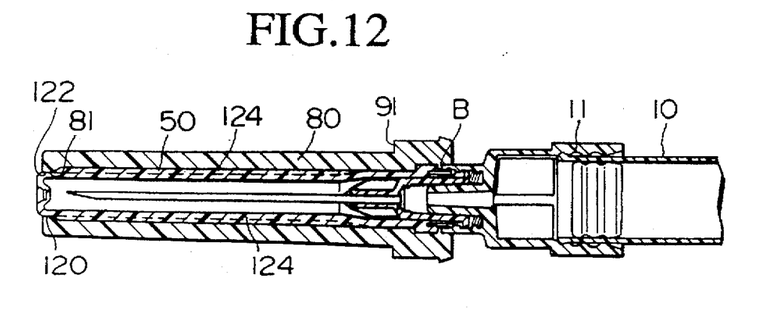
FIG. 12 shows the prefill syringe according to the eleventh embodiment of the present invention, wherein the components of the prefill syringe are shown in vertical cross-section.

FIG. 12 shows an eleventh embodiment of the present invention.

In this embodiment, a seal 122 which engages in an airtight fashion with the circumferential portion 120 at the tip of protector 50 is provided to communicating hole 81 which is formed in the closed end of the sheath-shaped cylindrical member 80 of the seventh embodiment shown in FIG. 8.

As in the ninth embodiment, seal 122 is composed of the entire area of the inner periphery of communicating hole 81.

In this embodiment, as in the ninth embodiment, after cylindrical member 80 has been attached so as to cover the area of engagement between protector 50 and needle holder 11, the influx of vapor or hot water from the outside via a space which may arise between the outer sides of protector 50 and the inner peripheral surface of cylindrical member 80 due to vertical ribs 124, ... formed to the outer surface of protector 50 is prevented. In other words, the design of this embodiment makes it possible to eliminate air remaining inside cylindrical member 80, while preventing the influx of vapor from the outside.

In the preceding embodiments, ting-shaped projections 22a were formed to the inner periphery of an elastic cylindrical member. These ring-shaped projections 22a are not absolutely necessary, however.

Further, the above embodiments described the case where 4 ring-shaped projections are provided, however, this is not a strict limitation but rather 6 or 8 ring-shaped projections may be provided.

Moreover, in the preceding embodiments, ring-shaped projection 22a was formed to be a semisphere in cross-section. However, the shape of ring-shaped projection 22a is not limited to this, but may form a square, triangle or half-ellipse in cross-section.

In addition, the preceding embodiments described the case where the present invention was employed in a general syringe. However, the present invention is not so limited, but may be suitably employed as a prefill syringe.

What is claimed is:

1. A prefill syringe provided with:
   a cylindrical cartridge into which a rubber stopper is inserted, having a needle holder at one end and a collar at the other end thereof, said needle holder being capable of receiving a needle assembly comprised of a cannula and a needle;
   wherein a cap for protecting the needle holder is attached to the needle holder situated at one end of the cartridge while leaving a gap between said needle holder and said cap so as to enable vapor or gas to enter into said cartridge during vapor or gas sterilization performed prior to filling said cartridge with a drug, and an elastic cylindrical member is externally engaged to span the needle holder and the cap so as to cover a gap formed between said needle holder and said cap in order to seal said cartridge after said cartridge has been filled with the drug.

2. A prefill syringe according to claim 1, wherein said needle holder comprises an outer peripheral surface, said cap comprises an outer peripheral surface, and said elastic cylindrical member comprises an inner periphery, said elastic cylindrical member further comprising one or more ring-shaped projections which contact the outer peripheral surface of the needle holder and the outer peripheral surface of the cap.

3. A prefill syringe according to claim 2, wherein the cylindrical member comprises a sheath having one end which is sealed and another end which is open.

4. A prefill syringe according to claim 3, wherein a communicating hole is formed in an end of the sheath.

5. A prefill syringe according to claim 4, wherein said cap comprises a tip, said prefill syringe further comprising a seal formed in an end of the sheath.

6. A prefill syringe according to claim 5, wherein said cylindrical member comprises a length and a stepped portion which is provided at a point along a length of the cylindrical member to the outer periphery thereof, said cylindrical member comprising a diameter at a tip of the cylindrical member which is different than a second diameter extending across an outer edge of the stepped portion.

7. A prefill syringe according to claim 3, wherein said needle holder comprises an outer peripheral surface, said cap comprises an outer peripheral surface, and said elastic cylindrical member comprises an inner periphery, said prefill syringe further comprising a syringe needle attached to a needle holder, a protector attached to the needle holder so as to cover the syringe needle, an elastic cylindrical member externally engaged to span across the needle holder and the protector in order to seal said prefill syringe after said prefill syringe has been filled with a drug, one or more ring-shaped projections which contact the outer peripheral surface of the needle holder and the outer peripheral surface of the protector are formed to the inner periphery of the cylindrical member, and the cylindrical member is formed in the shape of a sheath having an open end and a closed end.

8. A prefill syringe according to claim 7, wherein the cylindrical member comprises two ends, each of which are open.

9. A prefill syringe according to claim 8, wherein said cylindrical member comprises a length and a stepped portion which is provided at a point along a length of the cylindrical member to the outer periphery thereof, said cylindrical member comprising a diameter at a tip of the cylindrical member which is different than a second diameter extending across an outer edge of the stepped portion.

10. A prefill syringe according to claim 7, wherein said cylindrical member comprises a length and a stepped portion which is provided at a point along a length of the cylindrical member to the outer periphery thereof, said cylindrical member comprising a diameter at a tip of the cylindrical member which is different than a second diameter extending across an outer edge of the stepped portion.

11. A prefill syringe according to claim 7, wherein said elastic cylindrical member comprises a communicating hole which communicates the inside of the cylindrical member with the external environment and is formed in an end of the cylindrical member.

12. A prefill syringe according to claim 11, wherein said cylindrical member comprises a length and a stepped portion which is provided at a point along a length of the cylindrical member to the outer periphery thereof, said cylindrical member comprising a diameter at a tip of the cylindrical member which is different than a second diameter extending across an outer edge of the stepped portion.

13. A prefill syringe according to claim 11, wherein said protector comprises a tip, said prefill syringe further comprising a seal formed in an end of the cylindrical member.

14. A prefill syringe according to claim 13, wherein said cylindrical member comprises a length and a stepped portion which is provided at a point along a length of the cylindrical member to the outer periphery thereof, said cylindrical member comprising a diameter at a tip of the cylindrical member which is different than a second diameter extending across an outer edge of the stepped portion.

15. A prefill syringe according to claim 3, wherein said cylindrical member comprises a length and a stepped portion which is provided at a point along a length of the cylindrical member to the outer periphery thereof, said cylindrical member comprising a diameter at a tip of the cylindrical member which is different than a second diameter extending across an outer edge of the stepped portion.

16. A prefill syringe according to claim 2, wherein the cylindrical member defines a tube having ends which are open.

17. A prefill syringe according to claim 16, wherein said cylindrical member comprises a length and a stepped portion which is provided at a point along a length of the cylindrical member to the outer periphery thereof, said cylindrical member comprising a diameter at a tip of the cylindrical member which is different than a second diameter extending across an outer edge of the stepped portion.

18. A prefill syringe according to claim 2, wherein said cylindrical member comprises a length and a stepped portion provided at a point along a length of the cylindrical member to the outer periphery thereof, said cylindrical member comprising a diameter at a tip of the cylindrical member which is different than a second diameter extending across an outer edge of the stepped portion.

19. A prefill syringe according to claim 4, wherein said cylindrical member comprises a length and a stepped portion which is provided at a point along a length of the cylindrical member to the outer periphery thereof, said cylindrical member comprising a diameter at a tip of the cylindrical member which is different than a second diameter extending across an outer edge of the stepped portion.

20. A prefill syringe according to claim 1, wherein a stepped portion is provided at a point along is length of the cylindrical member to an outer periphery thereof, a diameter at a tip of the cylindrical member being different than a second diameter extending across an outer edge of the stepped portion.

* * * * *